United States Patent
Holub et al.

(10) Patent No.: US 7,416,752 B2
(45) Date of Patent: Aug. 26, 2008

(54) METHOD OF FORTIFYING SEEDS WITH AN ESSENTIAL FATTY ACID, FORTIFIED SEED AND FOOD PRODUCT

(75) Inventors: Bruce J. Holub, Guelph (CA); Arun Nagpurkar, Mississauga (CA)

(73) Assignee: Sharp Ingrained Functional Foods, Inc., Guelph, Ontario (CA)

( * ) Notice: Subject to any disclaimer, the term of this patent is extended or adjusted under 35 U.S.C. 154(b) by 443 days.

(21) Appl. No.: 10/916,336

(22) Filed: Aug. 11, 2004

(65) Prior Publication Data
US 2005/0147731 A1    Jul. 7, 2005

Related U.S. Application Data

(63) Continuation-in-part of application No. 10/752,897, filed on Jan. 6, 2004, now abandoned.

(51) Int. Cl.
*A23L 1/182* (2006.01)
(52) U.S. Cl. .................. 426/93; 426/455; 426/456; 426/507; 426/518; 426/629
(58) Field of Classification Search .............. 426/93, 426/629, 638, 640, 648, 607, 654, 455, 456, 426/507, 518
See application file for complete search history.

(56) References Cited

U.S. PATENT DOCUMENTS

| 4,277,502 | A |   | 7/1981 | Kurzius |
|---|---|---|---|---|
| 4,767,636 | A | * | 8/1988 | Ramos et al. ............... 426/291 |
| 5,962,062 | A |   | 10/1999 | Carrie et al. |
| 6,210,686 | B1 |   | 4/2001 | Bell et al. |
| 6,436,431 | B1 |   | 8/2002 | Hoffpauer et al. |
| 6,440,449 | B1 |   | 8/2002 | Hirschberg |
| 2002/0025983 | A1 |   | 2/2002 | Horrobin |
| 2003/0170371 | A1 |   | 9/2003 | Jobe et al. |

FOREIGN PATENT DOCUMENTS

| CA | 2064025 | 11/1991 |
|---|---|---|
| CA | 2452997 | 1/2003 |
| EP | 0 699 437 | 6/1996 |
| GB | 2203043 | 10/1998 |

(Continued)

OTHER PUBLICATIONS

A. J. Sinclair et al., "What is the Role of -Linolenic Acid for Mammals?", Lipids, vol. 37, No. 12 (2002), pp. 1113-1123.

(Continued)

*Primary Examiner*—Helen F Pratt
(74) *Attorney, Agent, or Firm*—Calfee, Halter & Griswold LLP

(57) ABSTRACT

A method is provided for fortifying a seed, grain, nut, bean, or the like with an essential fatty acid such as docosahexaenoic acid or eicosapentaenoic acid. Using the method, it is possible to produce seeds that can be used as a dietary source of that essential fatty acid. A seed that has been soaked in an aqueous mixture containing an essential fatty acid so as to become fortified with the fatty acid, and a food product formed using the seed are also provided.

59 Claims, 12 Drawing Sheets

PROCESS FLOW CHART

FOREIGN PATENT DOCUMENTS

| | | |
|---|---|---|
| JP | 61056102 A2 | 3/1986 |
| JP | 64002551 A2 | 1/1989 |
| JP | 1265854 A2 | 10/1989 |
| JP | 2000191421 A2 | 7/2000 |
| WO | WO 03003854 | 10/2003 |

OTHER PUBLICATIONS

E. A. Emken et al., "Dietary Linoleic acid influences desaturation and acylation of deuterium-labeled linoleic and . . . ", Biochimica et Biophysica Acta 1213 (1994), pp. 277-288.

G. C. Burdge et al., "Elcosapentaenoic and docosapentaenoic acids are the principal products . . . ", British Journal of Nutrition (2002), 88, pp. 355-363.

C. A. Francois et al., "Supplementing lactating women with flaxseed oil does not increase docosahexaenoic acid in their milk", Am J. Clin Nutr 2003, 77, pp. 226-233.

* cited by examiner

METHOD OF FORTIFYING SEEDS WITH AN ESSENTIAL FATTY ACID, FORTIFIED SEED AND FOOD PRODUCT

CROSS-REFERENCE TO RELATED APPLICATIONS

The present application is a continuation-in-part application of U.S. patent application Ser. No. 10/752,897, filed Jan. 6, 2004, now abandoned, the contents of which are hereby incorporated by reference herein.

FIELD OF THE INVENTION

The present invention relates generally to nutrition and fortified foods, and particularly to a method of fortifying a seed with an essential fatty acid, seeds so fortified and food products.

BACKGROUND OF THE INVENTION

An essential nutrient is a nutrient required by an animal for optimal health and functioning that must be obtained from dietary sources due to the fact that the animal does not have a metabolic mechanism for synthesis of the nutrient in sufficient quantities to meet body requirements. For example, certain fatty acids, such as omega-3 fatty acids, are considered essential for humans since the human body does not possess the enzymes required to produce them in sufficient quantities. As such, they must be obtained from other dietary sources. Most often, such nutrients are found in certain food sources and are ingested.

Essential omega-3 fatty acids, such as alpha-linolenic acid ("ALA"), docosahexaenoic acid ("DHA") and eicosapentaenoic acid ("EPA") have been implicated in maintaining human cardiovascular and mental health. Particularly, DHA is found in the membranes of brain, retina and nerve tissue, where it is physiologically essential for function, as well as in heart and blood cells.

ALA is readily found in certain plant and vegetable sources, such as flax seed, leafy green vegetables and nuts, and is therefore not typically lacking in the diet of most individuals. ALA, even when abundant in the diet, is readily oxidized, potentially resulting in a less effective uptake of ALA by the body than would be expected based on dietary levels of ALA. As well, ALA has no known direct function in the body, aside from acting as a precursor molecule for other polyunsaturated omega-3 fatty acids, such as DHA and EPA (Sinclair and Attar-Bashi *Lipids* (2002) 37:1113-1123.)

Although ALA may be converted by the body to DHA or EPA, this conversion requires multiple metabolic steps and occurs at an extremely low efficiency in humans, dogs, cats and birds. For humans, one study indicates that the conversion of ALA to DHA in human adults may be as low as 3.8% on average, based on conversion of deuterated dietary ALA to DHA (E. A. Emken et al., *Biochim Biophys Acta* (1994) 1213:277-288). A further study in young adult males detected no conversion of ALA to DHA over a 21 day period (G. C. Burdge et al., *Br J Nutr* (2002) 88:355-363). As well, subjects fed diets high in ALA did not show an increase in DHA levels, including the levels of DHA in breast milk in lactating women (C. A. Francois et al., *Am J Clin Nutr* (2003) 77:226-233). As a consequence, the level of DHA/EPA produced in the body as the result of conversion of dietary ALA may not be sufficient to meet the body requirements.

DHA and EPA are found in marine plants such as algae and in fish, and are most abundant in oily fish. As such, a diet rich in fish or marine plants may provide required quantities of DHA and EPA. Many individuals, however, have diets that are not rich in these foods and therefore may not get an adequate supply of DHA and EPA.

Similarly, infants and young children, for whom proper brain development is critical, may not have an adequate supply of these essential fatty acids in their diet. Although infants that are breast-fed will obtain some ALA, DHA and EPA through breast milk, the levels of DHA in the breast milk is dependent on the mother's dietary intake of this nutrient. Infants fed formula will be dependent on the level DHA and/or EPA in the formula.

Clearly then, there is a need to provide alternate dietary sources of DHA and EPA.

To this end, U.S. Pat. No. 6,436,431 (Hoffpauer et al.) discloses a method of using rice bran as a carrier to produce an admixture that is fortified with various nutrients, including omega-3 fatty acids from fish oil. However, addition of an oily substance to a powder or granular mixture can cause clumping and may result in uneven distribution of the fatty acid throughout the admixture.

Similarly, food supplements and pharmaceutical products containing omega-3 fatty acids have been developed. For example U.S. Pat. No. 6,210,686 (Bell et al.) discloses a yeast fiber-based supplement that may be enriched with omega-3 fatty acids. The supplement may be taken alone or may be added to foods such as beverages, baked goods, puddings, confections, snack foods, or frozen confections or novelties. However, yeast fiber is not a food component normally found in many of these types of foods, and addition of the supplement may alter the taste or consistency of prepared foods.

EP Patent Application No. 0699437 (Bruzzese) discloses a pharmaceutical composition that includes EPA and DHA formulated into gelatin capsules. Gelatin capsules are not always a convenient method of ingesting these essential fatty acids, particularly for infants, children or for adults that do not like to take medicines or pills.

U.S. patent application No. 20020025983 (Horrobin) describes pharmaceutical supplements containing Vitamin K and an essential fatty acid, including EPA or DHA, or a food stuff that has been fortified with Vitamin K and the essential fatty acid. The fatty acid is derived from an oil containing the fatty acid, such as fish oil in the case of DHA and EPA. However, the teaching of this reference does not overcome difficulties associated with addition of an oily substance to foodstuff.

U.S. Pat. No. 5,962,062 (Carrie et al.) describes a formulated milk product that contains a given ratio of various fatty acids, including DHA and EPA, which are obtained from marine organisms. However, such products are not suitable for individuals with milk allergies or intolerances, or who prefer not to consume animal byproducts.

Therefore, there remains a need for alternate, easily consumable food sources that allow for the inclusion of an adequate supply of DHA and other essential fatty acids in adult, child and infant diets.

SUMMARY OF THE INVENTION

In one aspect of the present invention there is provided a method of fortifying seed with an essential fatty acid, comprising mixing a quantity of the essential fatty acid with water to form a mixture; soaking the seed in the mixture so that an amount of the essential fatty acid is absorbed by the seed. In certain embodiments, the method further comprises dissolving the quantity of the essential fatty acid in a solvent prior to forming the mixture.

In another aspect of the present invention, there is provided a method of fortifying rice grain with an essential fatty acid selected from the group consisting of docosahexaenoic acid and eicosapentaenoic acid, comprising dissolving a quantity of the essential fatty acid in a solvent; mixing the solvent containing the essential fatty acid with water in a ratio of between about 1:99 and about 60:40 of solvent containing the essential fatty acid:water to form a mixture, the quantity of the essential fatty acid being sufficient to provide a final concentration in the mixture of between about 0.001% and 35%; soaking the rice grain in the mixture so that an amount of the essential fatty acid is absorbed by the rice grain.

In yet another aspect of the present invention, a method of fortifying plant matter with an essential fatty acid, comprising mixing a quantity of the essential fatty acid with water to form a mixture; soaking the plant matter in the mixture so that an amount of the essential fatty acid is absorbed by the plant matter.

In a further aspect of the present invention, there is provided a seed that is fortified with an essential fatty acid.

In still a further aspect of the present invention, there is provided plant matter that is fortified with an essential fatty acid, wherein the plant matter is fortified by soaking the plant matter in a mixture containing the essential fatty acid, the mixture comprising a solvent and water, the solvent containing the essential fatty acid.

In yet a further aspect of the present invention, there is provided a food product for consumption an animal, formed at least in part using a seed that is fortified with an essential fatty acid.

In yet another aspect of the present invention, there is provided a food product for consumption an animal, formed at least in part using seed that is fortified with an essential fatty acid, wherein the seed is fortified by soaking the seed in a mixture containing the essential fatty acid.

In still yet another aspect of the present invention, there is provided a food product for consumption an animal, formed at least in part using plant matter that is fortified with an essential fatty acid, wherein the plant matter is fortified by soaking the plant matter in a mixture containing the essential fatty acid.

In a further aspect of the invention, there is provided algae that is fortified with an essential fatty acid, wherein the algae is fortified by growing the algae in a medium comprising the essential fatty acid.

In yet a further aspect of the invention, there is provided a plant that is fortified with an essential fatty acid, wherein the plant is fortified by growing the plant in a medium comprising the essential fatty acid.

Therefore, in accordance with an aspect of the present invention an essential fatty acid is incorporated into a seed by soaking the seed in a solvent/water mixture containing the fatty acid. This allows for the introduction or the augmentation of natural levels of a particular fatty acid in the seed.

Generally, seeds will absorb aqueous solutions and components carried within those solutions via a passive transport mechanism. However, fatty acids, because of their long hydrophobic hydrocarbon chains, are not soluble in water, making such a mechanism for the fortification of a seed with an essential fatty acid a difficult process.

The inventors have found that by forming an oil and water mixture containing an essential fatty acid, and by soaking seeds in the mixture, the seeds will take up the fatty acid, thereby becoming fortified with the essential fatty acid. The total amount of the essential fatty acid absorbed by the seeds may be increased when a free fatty acid ("FFA") form of the essential fatty acid is used, rather than a triacylglycerol ("TAG") form.

The inventors have also found that by first solubilizing the essential fatty acid in an organic solvent and then mixing or dispersing the dissolved fatty acid in solvent into water, a water based mixture of the fatty acid can be formed that is useful for soaking seeds that are to be fortified with the chosen fatty acid. This approach may be more effective when a TAG form of the essential fatty acid is used.

This method is particularly useful for providing EPA/DHA enriched foods source that are not normally associated with these fatty acids, for example, rice, corn and soya. These foods can be easily consumed and are rich in the essential fatty acids DHA and EPA, which are most commonly found in fatty fish. The food source may not ordinarily contain DHA or EPA. Preferably the essential acid is plant-derived. When this is the case, the resulting seed may appeal to a wide population, including vegetarians.

The present invention also provides a plant-based food component including an essential fatty acid that may be ground into a fine powder. Advantageously, this allows for the inclusion of an oily substance into a variety of food products without the problems of clumping or phase separation normally associated with the addition of oils to dry foods or aqueous liquids.

Other aspects and features of the present invention will become apparent to those of ordinary skill in the art, upon review of the following description of specific embodiments of the invention and in conjunction with the accompanying figures.

BRIEF DESCRIPTION OF THE DRAWINGS

In the figures, which illustrate, by way of example only, embodiments of the present invention.

DETAILED DESCRIPTION

As used herein, the term "essential fatty acid" ("EFA") shall mean a nutrient required by an animal that cannot be synthesized at all by the animal or that cannot be synthesized by the animal in sufficient quantities required for optimal health of the animal, and must be obtained from dietary sources. The term includes fatty acids that are involved in the prevention, treatment and management of pathological conditions, including chronic diseases. The animal may be any animal, including a human, a dog, a cat or a bird.

The term "seed" shall mean a mature ovule of a flowering plant or any portion thereof. Therefore, the term "seed" shall include the edible kernel, endosperm, germ, bran or husk of a seed, grain, bean, legume or nut. For example, the term shall include white rice, which is the endosperm of the rice seed, and shall also include rice bran. The seed should be a food source for the animal that requires the essential fatty acid.

Figure 1:
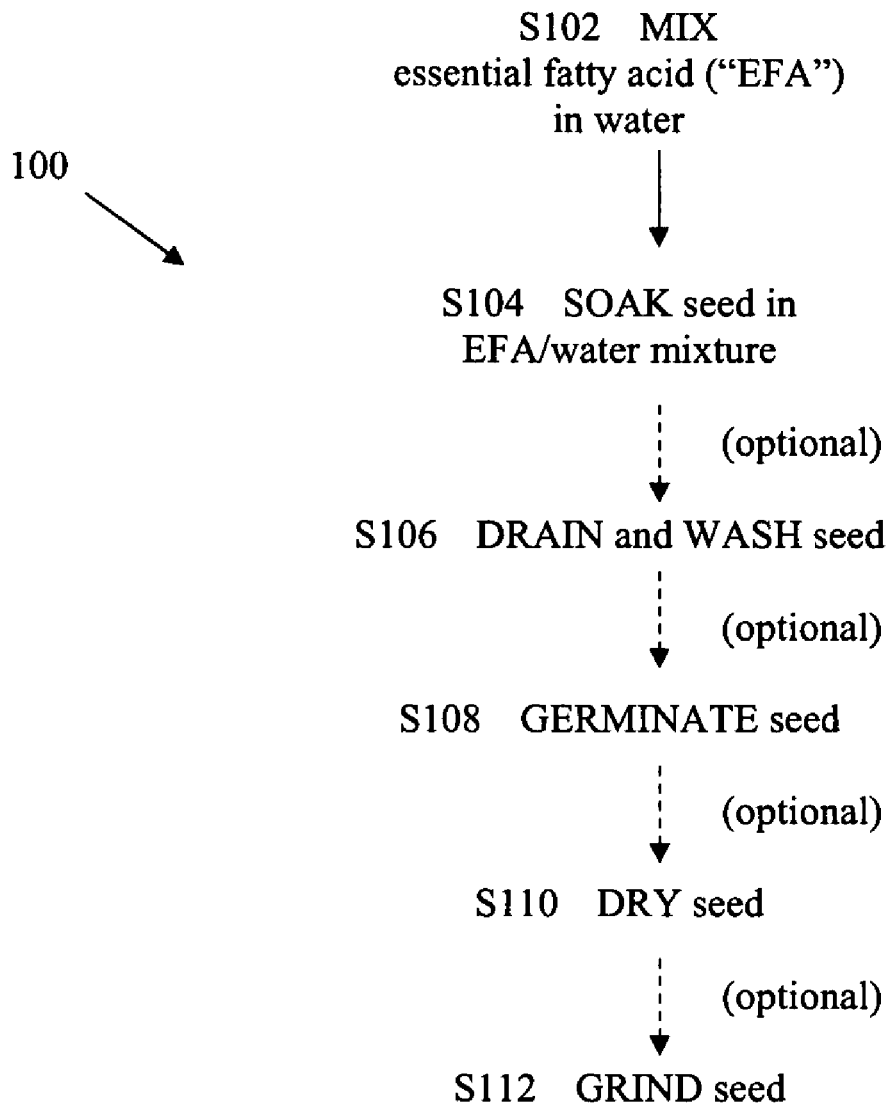
FIG. 1 is a process flow diagram, illustrating a method of fortifying a seed with an essential fatty acid, exemplary of an embodiment of the present invention.

FIG. 1 is a schematic representation of a method 100 of fortifying seed with an essential fatty acid. In step S102, a quantity of essential fatty acid is mixed with water to form a mixture of EFA and water, referred to herein as an EFA/water mixture. The term "mixture" refers to, and will be understood by a skilled person as, the composition resulting from the combination of the EFA in water. The term mixture includes a dispersion, a continuous or discontinuous emulsion and a microemulsion.

In forming the EFA/water mixture, since the essential fatty acid is not soluble in water, the essential fatty acid is dispersed in the water so as to form a dispersion or an emulsion, rather than dissolve in the water to form a single phase solution. Preferably, the essential fatty acid is added to water with vigorous mixing, such as by sonicating or vortexing the mixture to create an emulsion with fine droplet size. The essential fatty acid may be added in a drop-wise manner while the water is vigorously mixed. The resulting mixture may be mixed for a period of time after addition of the essential fatty acid so as to ensure adequate dispersion of the essential fatty acid in the water.

Example essential fatty acids include, but are not limited to, omega-3 fatty acids such as ALA, DHA, EPA, docosapentaenoic ("DPA") and stearidonic acid ("STA"), omega-6 fatty acids such as linoleic acid ("LA"), arachidonic acid ("AA"), gamma-linolenic acid and dihomo gamma-linolenic acid, and omega-9 fatty acids such as nervonic acid.

The essential fatty acid may already occur naturally within the seed that is to have the essential fatty acid incorporated. As a consequence, the natural levels of the essential fatty acid within that seed may be augmented by method 100. Alternatively, the essential fatty acid may be one that does not exist in the seed, whereby method 100 will result in the absorption of a novel fatty acid by the seed. As such, the term "fortifying" as used herein refers to the process of either increasing the levels of an essential fatty acid that is normally found in a seed to levels above the natural levels of that fatty acid in the seed, or of introducing a fatty acid not normally found within the seed to that seed. Similarly "fortified" describes a seed in which the levels of an essential fatty acid have been increased above the natural levels of that fatty acid normally found in the seed, or to which a fatty acid previously not found in the seed has been added.

The quantity of essential fatty acid may be in the form of a free fatty acid ("FFA"), in which the acid moiety of the fatty acid is not directly covalently bonded to a backbone molecule of a fat. This form of the EFA may be preferred, as it appears to be more readily taken up by the seed during fortification using the present methods.

Free fatty acids forms of many essential fatty acids are commercially available. As well, the free fatty acid form of the essential fatty acid may be obtained from a simple or mixed triacylglycerol containing the fatty acid, using standard techniques known in the art. For example, the FFA may be obtained by saponification of the triacylglycerol, or by enzymatic treatment of the triacylglycerol with an appropriate lipase enzyme, or by cleavage on an ion exchange chromatography column.

Briefly, a saponfication reaction may be performed by dissolving a tri-, di-, or monoacylglycerol containing the desired fatty acid in a solvent such as ethanol, and treating it with a strong base, for example NaOH. The unreacted reagents can be removed by extraction of the free fatty acid using a suitable solvent that is immiscible with the solvent used for the reaction, for example by extraction with hexane, followed by evaporation of the solvent to yield the free fatty acid.

Enzymatic digestion, for example, digestion with lipase, can be used to release a free fatty acid form of an EFA from an acylglycerol as follows. The acylglycerol is incubated with lipase in a suitable buffer, for example containing detergent to solubilize the acylglycerol, at an appropriate temperature for the enzyme to function, but which will result in minimal oxidation of the fatty acid. Upon completion of the enzymatic digestion reaction, the free fatty acid may be obtained by extraction from the reaction solution.

Alternatively, the quantity of essential fatty acid may be incorporated into a fat or oil, for example by esterification of the acid group with a hydroxy group of a backbone molecule of the fat, such as the glycerol moiety of a triacylglycerol, a diacylglycerol, a monoacylglycerol or a phospholipid. The terms triacylglycerol ("TAG"), diacylglycerol ("DAG") and monoacylglycerol ("MAG") may be interchanged with triglyceride ("TG"), diglyceride ("DG") and monoglyceride ("MG"), respectively.

Furthermore, the quantity of essential fatty acid may be incorporated into a derivatized form of a free fatty acid, which is any free fatty acid that is covalently bonded to an additional functional group, for example through the carboxylic acid moiety of the free fatty acid. The additional functional group may be any functional group, including an amino acid or carbohydrate moiety. A derivatized form of a free fatty acid includes an alkyl ester, for example a methyl ester or an ethyl ester, and also includes an ascorbyl ester.

In a preferred embodiment, the quantity of essential fatty acid used in method 100 is docosahexaenoic acid or eicosapentaenoic acid. The essential fatty acid may for example be docosahexaenoic acid obtained from an algal source, such as the algae *Crypthecodinium cohnii*. Conveniently, the use of algal- or plant-derived essential fatty acids allows for creation of an easily consumable dietary source of an essential fatty acid that is not animal derived. The essential fatty acid may be obtained from an organism genetically engineered to produce the particular fatty acid. Such a genetically engineered organism may be one that does not normally produce the essential fatty acid, or it may be one that normally produces the essential fatty acid at low levels, but has been genetically modified to produce higher levels of the essential fatty acid.

Use of the free fatty acid form of the essential fatty acid may be advantageous, as the results presented herein indicate that fortification by the present methods, using the FFA form of an EFA results in more efficient uptake of the EFA by the seed compared to use of fish oil containing esterified forms of an EFA, such as the TAG form or the phospholipid form.

The amount of the essential fatty acid dispersed in the water will vary, depending on the form of essential fatty acid that is to be used, the volume of water and seed that is to be used, the nature of the particular seed to be in which the essential fatty acid is to be incorporated and the desired end concentration of the essential fatty acid into the particular seed. The desired end concentration of essential fatty acid will be determined in part by the effect of addition of the essential fatty acid on the flavour of the resulting fortified seed. In one embodiment, the end concentration of essential fatty acid is between about 1 and 50 mg of DHA and/or EPA per g of powdered seed.

An appropriate ratio of essential fatty acid:water used to form the EFA/water mixture can be readily determined by a skilled person using minimal routine experimentation. In one embodiment, the concentration of the essential fatty acid in free form or of an esterified fat containing the essential fatty acid in the final EFA/water mixture is between about 0.001% and about 35% when an FFA form is used, and between about 0.001% and about 10% when a triacylglycerol is used. In one embodiment, the concentration is between about 0.15 and about 20%. In another embodiment the concentration is between about 0.15 and about 5%. In yet another embodiment the concentration is between about 0.15 and about 1.2%.

Optionally, an antioxidant may be included with the essential fatty acid when forming the EFA/water mixture, so as to help minimize oxidation of the essential fatty acid. The antioxidant may be an antioxidant typically used to prevent rancidity of fats or oils, and includes water soluble or fat soluble Vitamin C, Vitamin E, tocopherols, anothocyanin, resveratrol, lycopene, pycnogenol, isoflavones, lutein, and carotenoids.

The mixture may be prepared at any temperature at which the EFA is stable. For example, water at room temperature (20 to 22° C.) may be used to form the mixture, or the water may be heated, for example, to 25 to 40° C. prior to forming the mixture.

In step S104, seed is soaked in the mixture such that the seed absorbs some of the essential fatty acid so as to become fortified with the essential fatty acid. The seed may be whole intact seed, or it may be processed before soaking so as to break up the whole seed into fragments. In various embodiments of the method, the seed may be flax, fenugreek, edible beans, chick pea, kidney bean, soya bean, nuts, peanut, walnut, almond, white rice, brown rice, wild rice, oats, wheat, corn, barley, hemp, rye, canola, sesame, millet, alfalfa, spelt, amaranth, kamut, quinoa, sorgum, buckwheat, wheat germ, wheat bran, rice bran, oat bran, cumin, oatmeal, popcorn, oil seed, pulses, legumes or lentils.

Enough EFA/water mixture should be used to properly cover the seed, such that all the seeds will be properly exposed to the essential fatty acid. In one embodiment, the volume ratio of seeds to EFA/water mixture is between about 0.5:1 and about 1:10. In another embodiment, the volume ratio of seeds to EFA/water mixture is between about 1:1 and about 1:6.

The seed may be soaked for a period of time long enough to effect the absorption of an appropriate amount of the essential fatty acid by the seed. The essential fatty acid is absorbed by the seed such that it is removed from the mixture and is no longer available for absorption. Soaking time will vary depending on the seed, the concentration of essential fatty acid in the EFA/water mixture, and the desired concentration of essential fatty acid to be absorbed by the seed. Soaking time can readily be determined by a skilled person with minimal exercise of routine experimentation. In various embodiments, soaking time may be between 0.5 and 72 hours, between 1 and 24 hours, or between 3 and 18 hours.

The total amount of essential fatty acid that has been absorbed by the seed as a result of steps S102 and S104 may be determined by standard methods known in the art, for example, by gas chromatography, liquid chromatography, capillary chromatography or gas-liquid chromatography. The total amount of EFA taken up by the seed will depend on the conditions used, such as the concentration of EFA in the mixture, the form of the EFA used, the soaking temperature and time, the type of seed, and the seed:mixture ratio. For example, using a saponified fish oil in the present methods, in which the EFA has been processed to the FFA form, it is possible to obtain between 10 and 1500 mg per 100 g of fortified seed, or between 100 and 1000 mg of EFA per 100 g of fortified seed.

Soaking should be done under conditions that are conducive to maintaining the integrity of the seed and the fatty acid. Generally, soaking will be done at a temperature between 0° C. and 50° C., preferably at room temperature or lower. However, for certain essential fatty acids, for example, certain polyunsaturated fatty acids that are extremely sensitive to light, oxygen and/or high temperature, soaking should be done in the absence of light under reduced oxygen conditions at room temperature or lower. Care should be exercised to ensure that the seed is not soaked long enough to leach other nutrients into the EFA/water mixture. Similarly, the seed should not be soaked long enough to loose its physical properties (e.g. texture and consistency).

In step S106, the EFA/water mixture is drained and the seed is washed after soaking is complete, to remove excess fatty acid. Multiple rounds of washing using clean water may be done to ensure complete removal of the excess mixture. However, in some instances, more essential fatty acid may be absorbed by the seed without washing, and therefore it may be desirable to eliminate the washing step.

Optionally, the seed may be germinated in step S108 prior to drying. Germination time will depend on the particular seed, fatty acid source and germination conditions used. Under some conditions, germination may maximize the amount of essential fatty acid absorbed by the seed. In one embodiment, the seeds are germinated under moist conditions at room temperature for between 6 hours and 7 days, between 1 and 7 days, more preferably between 1 and 3 days, more preferably between 12 and 72 hours.

Once the seed has been soaked and optionally drained and washed, the seed may optionally be dried in step S110 so as to prevent mildewing of the seed. Drying may be achieved by standard methods known in the art, using for example low to moderate heat or by freeze-drying. If drying is done with heat, a dessicant may be used. Drying may also be done with circulating air.

Once the seed, or the germinated seed, has been dried, it may be ground into a powder if desired in step S112. Grinding may be done using conventional methods that are known to a person skilled in the art.

Figure 2:
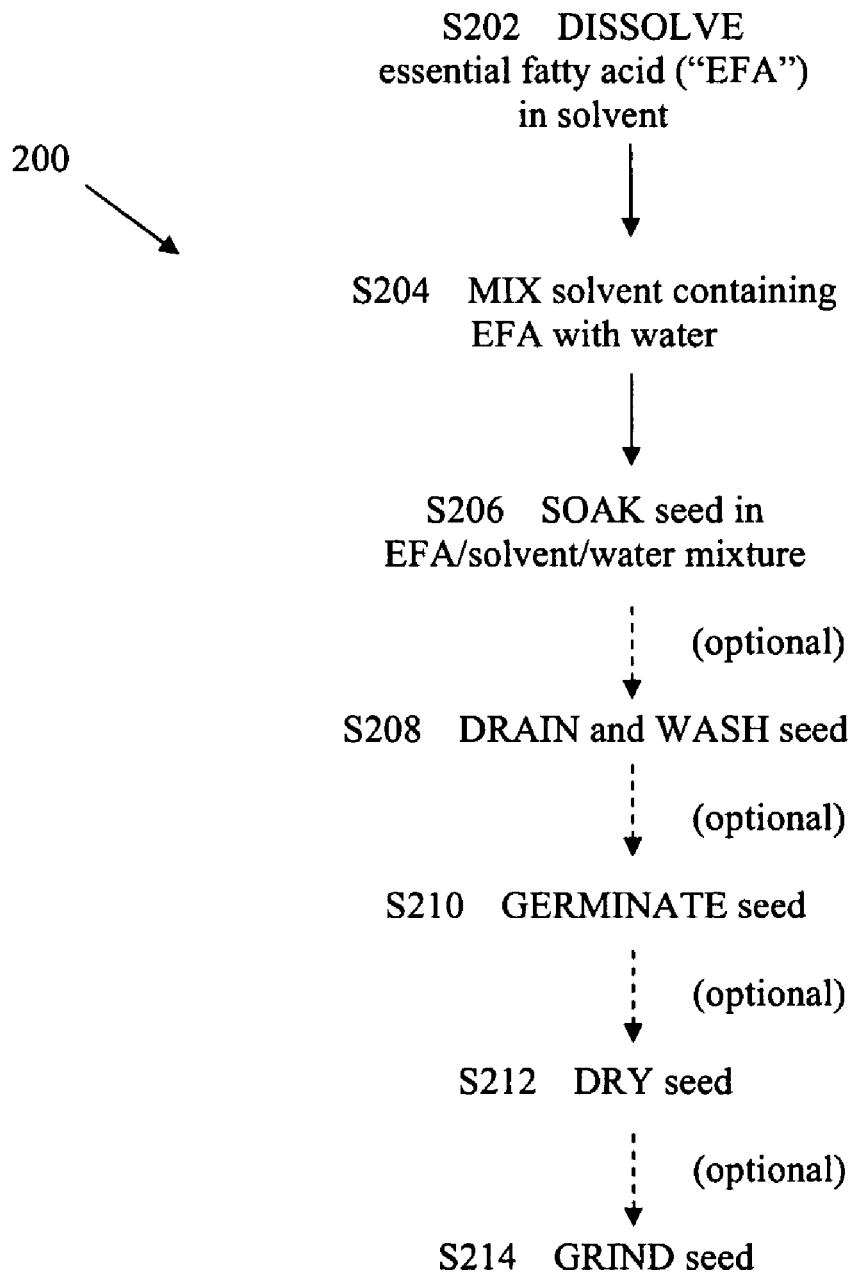
FIG. 2 is a process flow diagram, illustrating a method of fortifying a seed with an essential fatty acid, exemplary of an embodiment of the present invention.

Fatty acids are not soluble in water. Therefore, to increase the amount of essential fatty acid that is taken up by the seed, a solvent may be used, particularly where the fatty acid is conjugated in triacylglycerol form that is not readily taken up using the above method. Thus, in one embodiment there is provided a method 200 as depicted in FIG. 2. In step S202, a quantity of the essential fatty acid is dissolved in a solvent, either by addition of the solvent to the essential fatty acid, or by addition of the essential fatty acid to the solvent.

The solvent may be any solvent in which the essential fatty acid is soluble. Since fatty acids in general are not soluble in water or aqueous solution, the solvent will preferably be an organic solvent. As well, the solvent is preferably suitable for ingestion by the animal for which the fortified seed is intended, for example a human. The solvent itself may or may not be miscible with water. In one embodiment, the solvent is ethanol. In one embodiment an emulsifier is used in addition to the solvent. In another embodiment the solvent is an emulsifier. Preferably, the emulsifier is also suitable for ingestion by a human. In one embodiment the emulsifier is lyso-lecithin or lecithin. In another embodiment the emulsifier is a detergent, for example, TRITON X-100™ (t-octylphenoxypolyethoxyethanol). Where an emulsifier is used, the EFA may be mixed with the water and the emulsifier may be added to the mixture once the mixture is formed, rather than being added directly to EFA prior to the addition of water. Alternatively, the emulsifier may be mixed with the EPA prior to mixing with water.

The concentration of the essential fatty acid in the solvent will vary, depending on the form of essential fatty acid that is to be used, the solubility of the essential fatty acid in the particular solvent, the ratio of solvent to water that is to be used, the nature of the particular seed to be in which the essential fatty acid is to be incorporated and the desired end concentration of the essential fatty acid into the particular seed.

An appropriate ratio for a given essential fatty acid/solvent/seed combination can be readily determined by a skilled person using minimal routine experimentation, as described for the EFA/water mixture of method 100 set out above.

Once the quantity of essential fatty acid is dissolved in the solvent, the solvent, now containing the essential fatty acid, is mixed with water so as to form an EFA/solvent/water mixture, in step S204.

The ratio of solvent containing the essential fatty acid to water may vary. The water content should be high enough to properly effect the absorption of the fatty acid by the seed. Too high a concentration of organic solvent may disrupt the integrity of the seed. Preferably, the ratio is between 1:99 and 60:40, more preferably between 5:95 and 20:80.

The remainder of method 200 is performed as described above for steps S102 to S112. As with step S108, the seed may be washed after soaking. Washing removes excess solvent, minimizing the intake of the solvent by the animal that is to consume the seed. However, as stated above, washing may reduce the amount of essential fatty acid absorbed by the seed.

A skilled person will be able to readily determine, using minimal routine experimentation, whether it is advantageous to use method 100 or 200, depending on the particular seed, solvent, and concentration and form of EFA that is to be used.

Advantageously, methods 100 and 200 result in whole seed or powdered seed fortified with an essential fatty acid. Such seed or powder may be consumed directly or incorporated as a conventional ingredient into other food products for consumption by the animal, providing a convenient increased dietary supply of the essential fatty acid. For example, flax that is fortified with DHA may be consumed directly or added as a topping to cereal or salad. As well, flax fortified with DHA may be ground to a powder and used in baked products, such as bread, or it may be added to products such as infant formula or meal replacement drinks and bars. Food products that may contain the seed so fortified include breakfast cereals, bread, bread mixes, pasta, cookies, cookie mixes, cake, cake mixes, nutrition bars, meal replacement powders and mixes, nutrition supplements, pancake mix, waffle mix, chocolate bars, snack bars and the like. As well, the seed may be incorporated into animal feed and pet food.

For example, bread may be baked with 2.5% to 10% (w/w) of fortified ground flax that has been fortified with approximately 3.5 mg of DHA per g of powdered flax. A resulting 25 g slice of bread contains between about 2.2 and 8.8 mg of DHA. Similarly, a 20 g cookie may be made with 25% (w/w) flax powder containing approximately 3 mg of DHA plus EPA per g of flax powder contains approximately 15 mg of combined DHA and EPA.

For example, bread fortified with EPA and DHA may be prepared according to the following recipe:

| Ingredients | | | |
|---|---|---|---|
| unbleached flour | 9080 g | starter with yeast | 454 g |
| purified water | 3178 ml | honey | 227 g |
| EFA fortified flax powder | 227 g | salt | 84 g |
| olive oil | 200 g | | |

Directions

Blend flour and water to form a dough mixture; add remaining ingredients to dough mixture; prepare dough for baking as required, including kneading, shaping and proofing; bake at 450° F.; makes 16 loaves.

Similarly, cookies may be prepared, for example, by adding 100 g of EFA fortified flax powder to 450 g of commercially available cookie mix and then preparing the mix in accordance with the instructions.

The fortified seed obtained using methods 100 and 200 may optionally be germinated, as in steps S108 and S210, without subsequent drying, so as to form sprouts. Such sprouts may be used as greens in salads and sandwiches or to produce greens for use in drinks, for example cereal grass juices. A skilled person will understand the conditions required to germinate and sprout a particular type of seed used in method 100 or 200. The sprouts produced typically contain some of the essential fatty acid used to fortify the seed prior to sprouting, indicating that the incorporated essential fatty acid is being utilized by the seed.

The sprouts may also be used to grow into plants using hydroponic growth techniques that are known in the art. The resulting plants fortified with the essential fatty acid can be used directly as a dietary source of the essential fatty acid, or it may be further processed into a food product for consumption. Preferably, the sprouts are cultured in growth medium containing an FFA form of the EFA.

The above description is given in terms of fortifying a seed. However, it will be apparent that the above description may be readily adapted to apply to plant matter, such plant matter being any portion or part of a plant whether intact or processed into fragments. For example, the above method can be used to fortify roots, tubers, or the rhizome of a plant with an essential fatty acid. In various embodiments, herbs and spices may be fortified using the above method. For example, turmeric may be fortified with EPA and DHA, turmeric being powder derived from the rhizome of the plant *Curcuma domestica*.

Produce from plants, such as tomato or cabbage, or algae grown hydroponically may be fortified with the essential fatty acid. Briefly, in hydroponic methods, plants are grown with a liquid growth medium containing nutrients, rather than in soil. The nutrients that are typically obtained by the plant from soil are added to the growth medium, which is supplied to the plant roots, either by submerging the roots in the medium, by spraying or misting the roots with the medium, or by dripping or periodically flooding the medium onto the roots. If the roots are submerged in the medium, a pump may be used to aerate the medium so that the plant can obtain the necessary oxygen through its roots. A particulate support, such as gravel may be used, or other means to support the plants, such as with a trellis or wire system, may be used. To produce plants, including the fruits borne by the plant, or algae that are fortified with an essential fatty acid, a mixture of water and the EFA may be added to the hydroponic growth medium, with or without the addition of solvent. The essential fatty acid is thus available in the growth medium such that it may be taken up by the plant or algae, potentially for incorporation into the cellular membranes. Certain algae, for example, *Crypthecodinium cohnii*, naturally produce DHA. Growing an algae that does not naturally produce a given EFA in medium containing the EFA can result in an algae source fortified with the EFA. Methods of growing algae are known in the art, for example, as disclosed in U.S. Pat. No. 5,547,699 (Iizuka et al.), which is herein incorporated by reference.

The following experiments are illustrative of performing methods 100 and 200 and resulting fortified seed, and do not limit the broad aspects of the method or seed as disclosed herein.

EXAMPLES

Generally, the experiments were performed as follows.

Solutions were prepared with either fish oil (referred to as "FO" or "TAG" to indicate that the EFA is in triacylglycerol form), the FO containing 40% EPA and 20% DHA (Clear Water™ or See Yourself Well™) or with free fatty acid DHA (Nuchek), as specified. Where indicated, Clear Water™ fish oil was saponified to produce the FFA forms of the EFAs (Pilot Plant Corp., Saskatoon).

Seeds used were flax (Bob's Red Mill™), basmati rice (Veetee™) and fenugreek (No Name™).

For experiments using flax and fenugreek, solutions were prepared by adding quantities of the example essential fatty acid (between 0.15 and 3.0 g) for final concentrations of between 0.15% and 3% (w/v), in 5 ml of water or in 5, 10 or 20 ml of ethanol, and vortexed for 1 minute. Solutions were then made up to a final volume of 100 ml with water and vortexed for an additional minute. 50 g of flax or fenugreek seeds were soaked in the solution for approximately 12 hours at 22-23° C. In some instances, seeds were then washed 5 times with 180 ml volumes of clean water and drained. Seeds were in some cases germinated in a humid environment for between 0 and 168 hours. Seeds were then dried at 60-65° C. to a constant weight and in some cases ground to powder using a grinder that does not generate excessive heat. Amounts of EPA, DHA, linoleic acid ("LA"), alpha linolenic acid ("ALA") in the seeds were determined by gas chromatography methods. The amount of DHA and EPA as a percentage of total fatty acid content in the seed were also determined.

The experiments performed with rice were performed as described above, with the quantity of FO or FFA adjusted so as to obtain comparable final concentrations in the soak mixture. The EFA was added to 3.75 ml of water or 3.75, 7.5 or 15 ml of ethanol as indicated, and the final mixture volume was 75 ml. The rice was soaked under conditions described for 6 hours.

Where saponified fish oil was used, the saponification was reaction was carried out in a three neck flask fitted with a condenser and temperature was maintained using a water bath. The required amount of 95% ethanol and 136 mg of NaOH were added to the flask with stirred until complete dissolved. 1.0 g FO was transferred to the mixture and refluxed under nitrogen for 1.5 h at 40° C. After 1.5 h of refluxing, the saponified mixture was transferred to a glass beaker and allowed to come to room temperature (22-25° C). The unsaponifiable matter present was extracted with hexanes (×2) and discarded. The aqueous phase was acidified to pH 2.0 using 3N HCl. After acidification, hexanes was added to the aqueous phase and thoroughly mixed. The mixture was transferred to a separatory funnel and the lower aqueous layer was removed and discarded. The upper hexane layer was evaporated to recover the saponified FFA fish oil in FFA form.

The results of some individual experiments are set out in the following examples, with accompanying figures.

Fenugreek

Figure 3A:
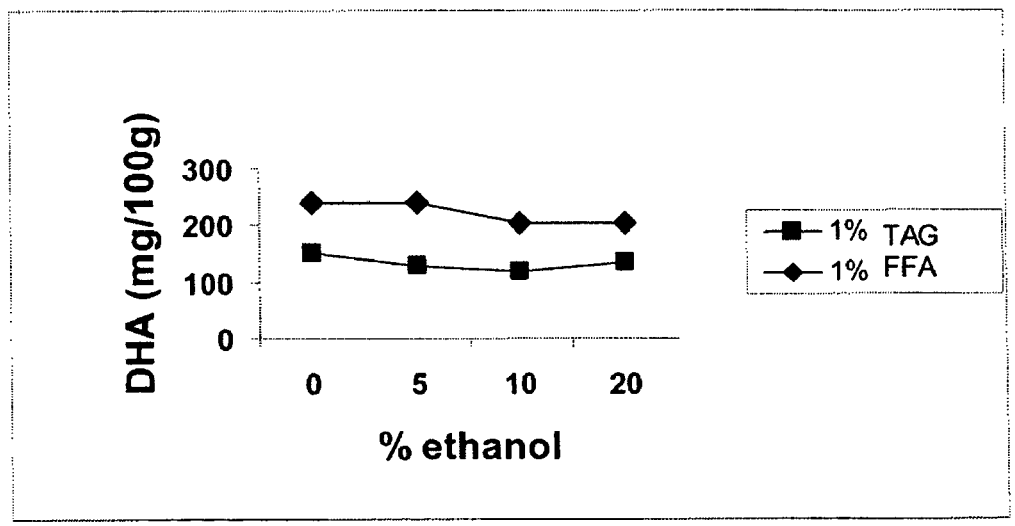
FIG. 3A is a graph illustrating uptake of DHA in fenugreek from soaking in a mixture containing 1% fish oil which is either unsaponified (TAG) containing 0.2% DHA or saponified (FFA) containing 0.18% DHA.
Figure 3B:
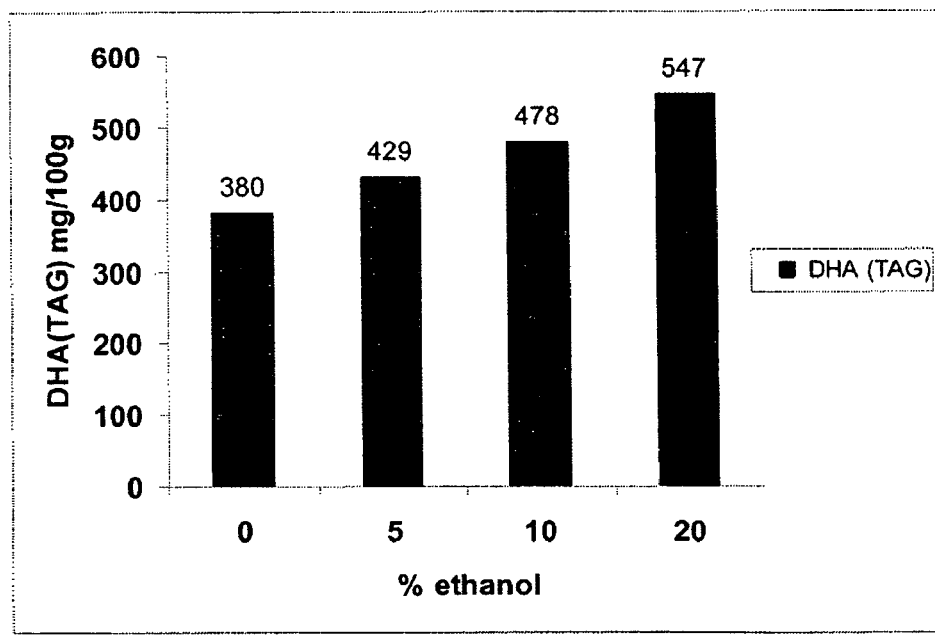
FIG. 3B is a graph illustrating the effect of ethanol on uptake of 0.6% DHA (TAG) by fenugreek.

As shown in FIG. 3A, the saponified form of DHA derived from fish oil (FFA) was more readily taken up by the seed than the esterified DHA in TAG form (TAG). Increase in ethanol concentration had little to no effect, or a slight negative effect on DHA derived from fish oil, either saponified or unsaponified at lower concentrations, but had a slight positive effect on uptake of unsaponified DHA at higher concentrations (FIG. 3B).

Figure 3C:
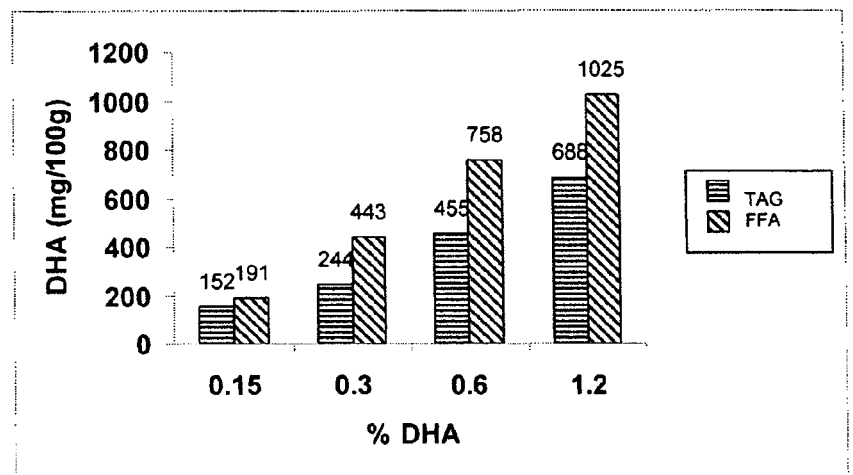
FIG. 3C is a graph illustrating the effect of concentration of DHA in the soak mixture on uptake of DHA in fenugreek.

Generally, increasing the concentration of fish oil, either in saponified or unsaponified form increased the total amount of DHA taken up by the fenugreek seed (FIG. 3C).

Figure 3D:
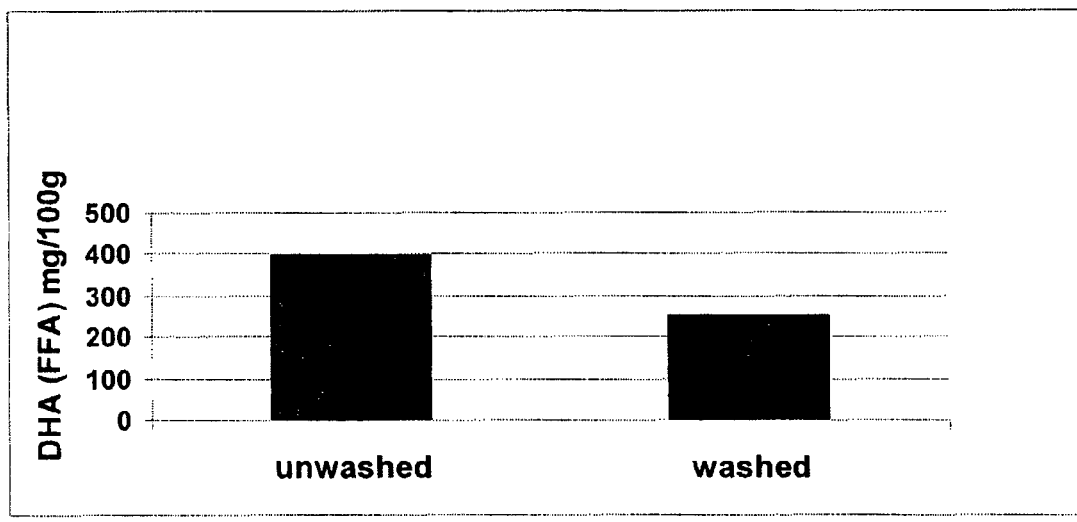
FIG. 3D is a graph illustrating the effects of washing fenugreek seeds fortified with DHA.

Washing reduced the final amount of DHA incorporated in the fenugreek seed (see FIG. 3D).

Flax

Figure 4A:
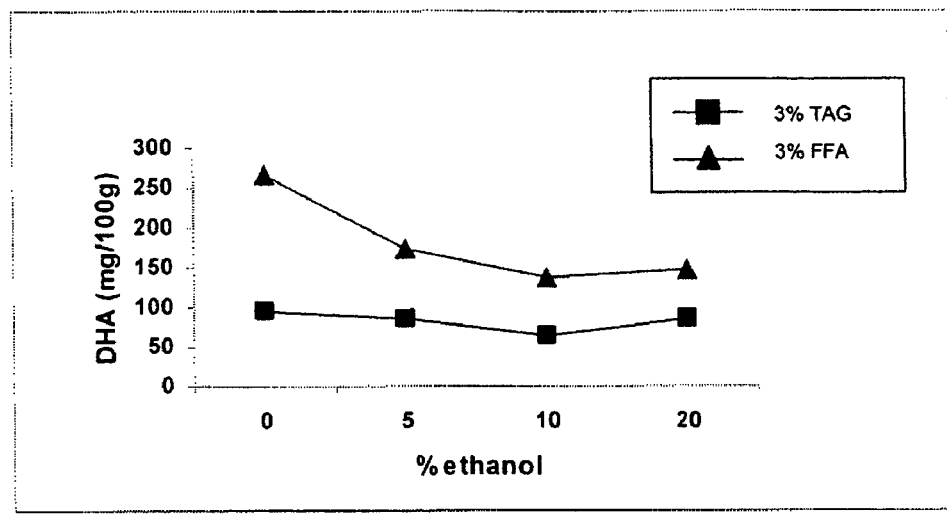
FIG. 4A is a graph illustrating uptake of DHA in flax from soaking in a mixture containing 3% fish oil which is either unsaponified (TAG) containing 0.6% DHA or saponified (FFA) containing 0.5% DHA.
Figure 4B:
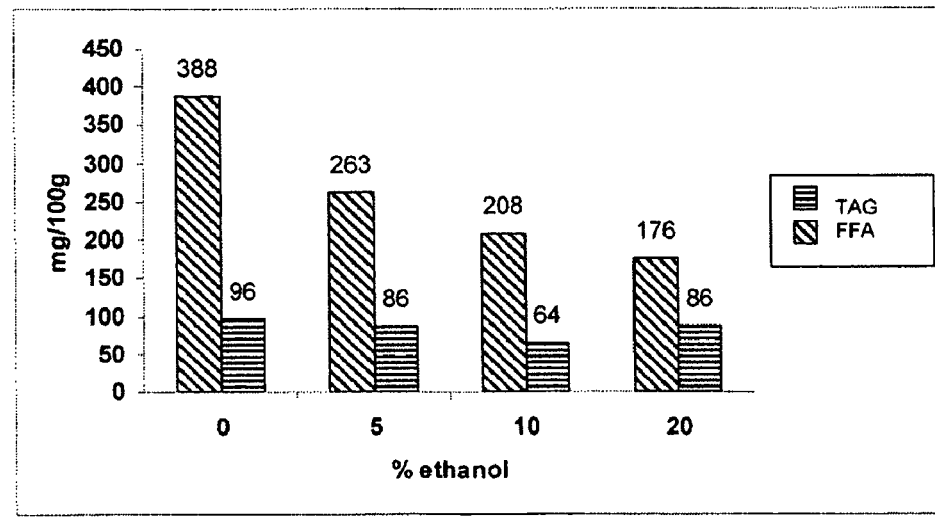
FIG. 4B is a graph illustrating the effect of ethanol on uptake of DHA (TAG) and DHA (FFA) by flax.
Figure 4C:
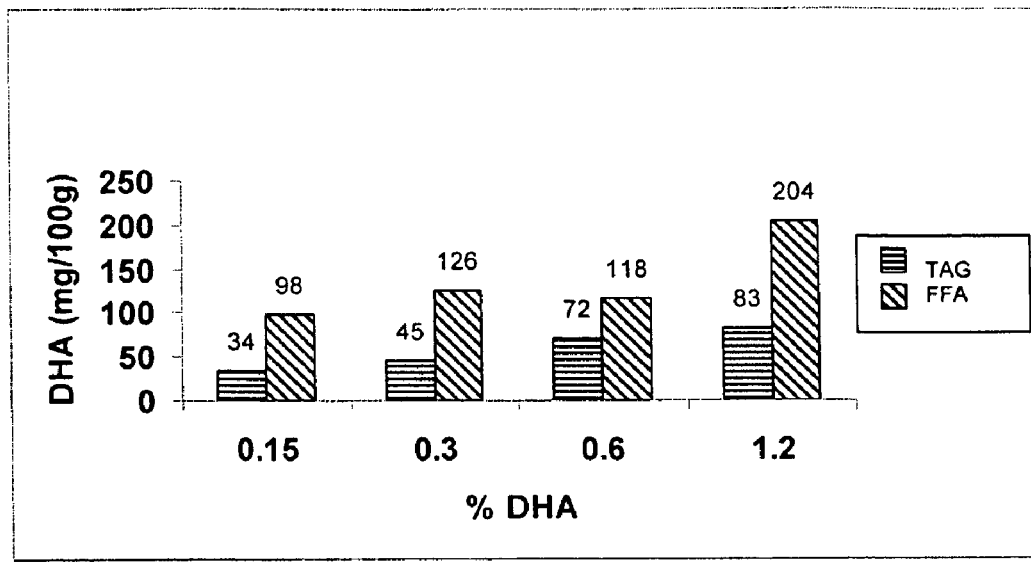
FIG. 4C is a graph illustrating the effect of concentration of DHA in the soak mixture on uptake of DHA in flax.

The results obtained with flax indicate that, as with fenugreek, more DHA from saponified FO was taken up than from unsaponified FO (FIG. 4A). Ethanol had little or no effect on the uptake of DHA in unsaponified FO, but uptake of DHA derived from saponified FO decreased as ethanol concentration increased (FIG. 4B). As seen with fenugreek, increasing the concentration of fish oil, either in saponified or unsaponified form increased the total amount of DHA taken up by the flax seed (FIG. 4C).

Basmati Rice

Figure 5A:
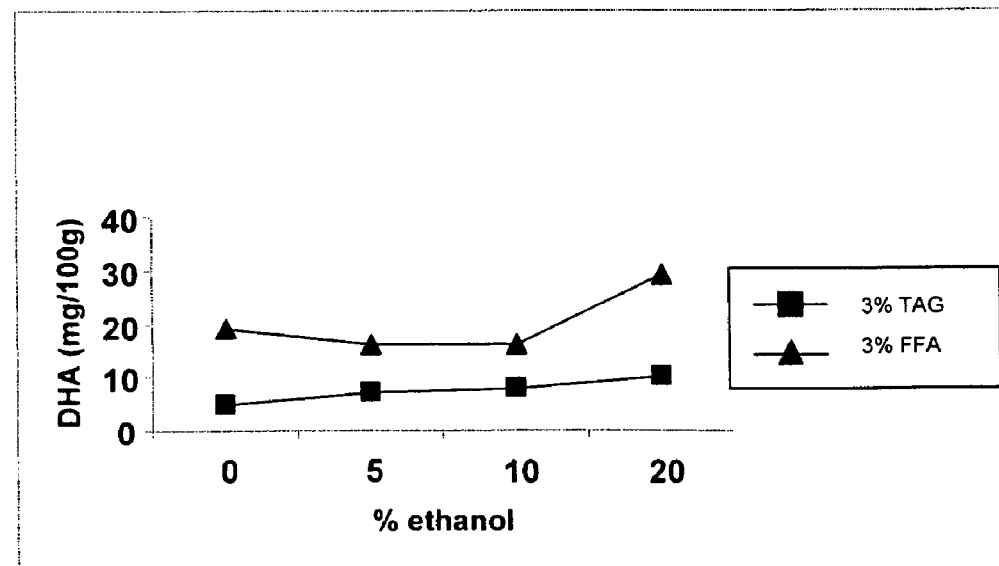
FIG. 5A is a graph illustrating uptake of DHA in basmati rice from soaking in a mixture containing 3% fish oil which is either unsaponified (TAG) containing 0.6% DHA or saponified (FFA) containing 0.5% DHA.
Figure 5B:
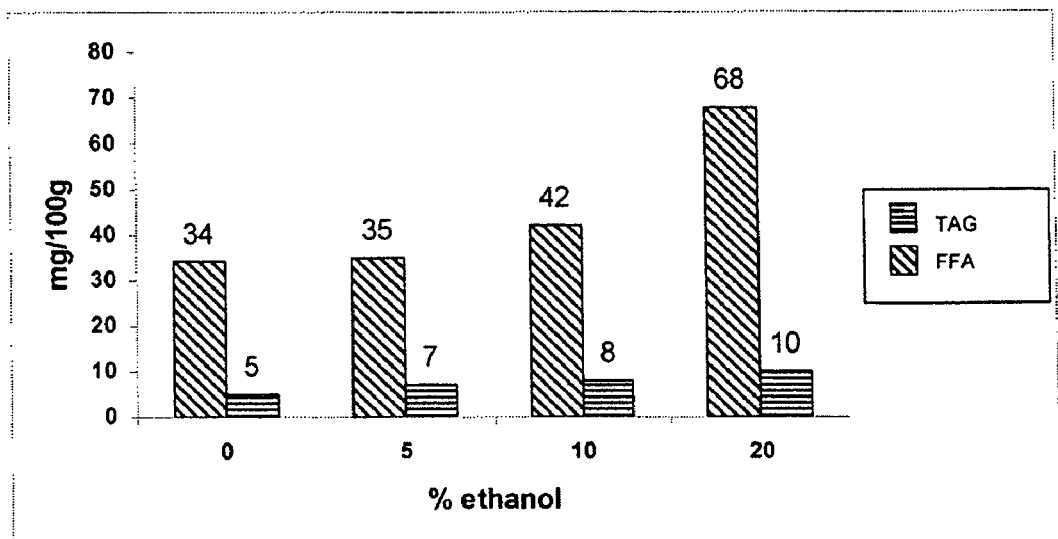
FIG. 5B is a graph illustrating the effect of ethanol on uptake of DHA (TAG) and DHA (FFA) by basmati rice.
Figure 5C:
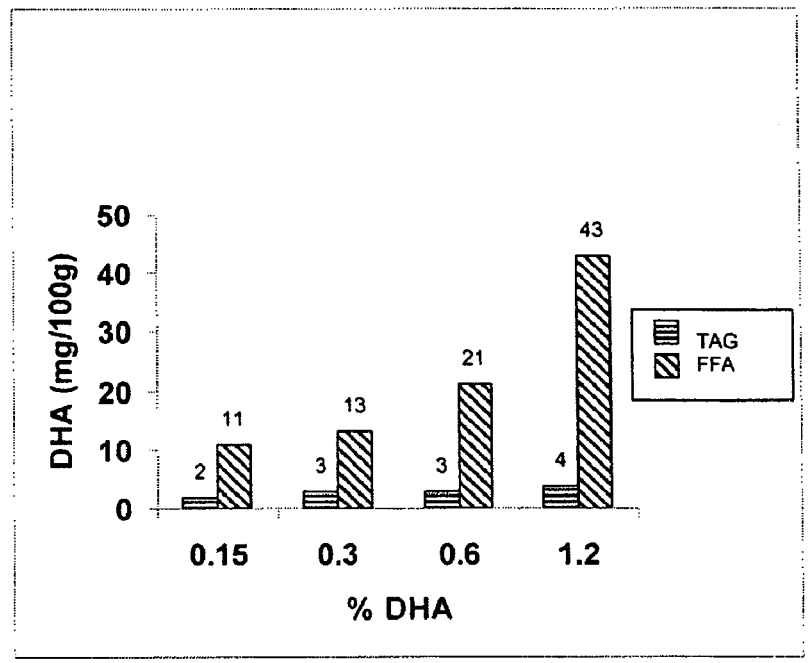
FIG. 5C is a graph illustrating the effect of concentration of DHA in the soak mixture on uptake of DHA in basmati rice

With rice, it was observed that the saponified fish oil was taken up more readily than unsaponified, and that 20% ethanol concentration resulted in significant increase in absorption of unsaponified FO (FIGS. 5A-B). The results of increasing concentration of DHA, either in FFA or TAG form is shown in FIG. 5C.

Germination of Fenugreek

Figure 6A:
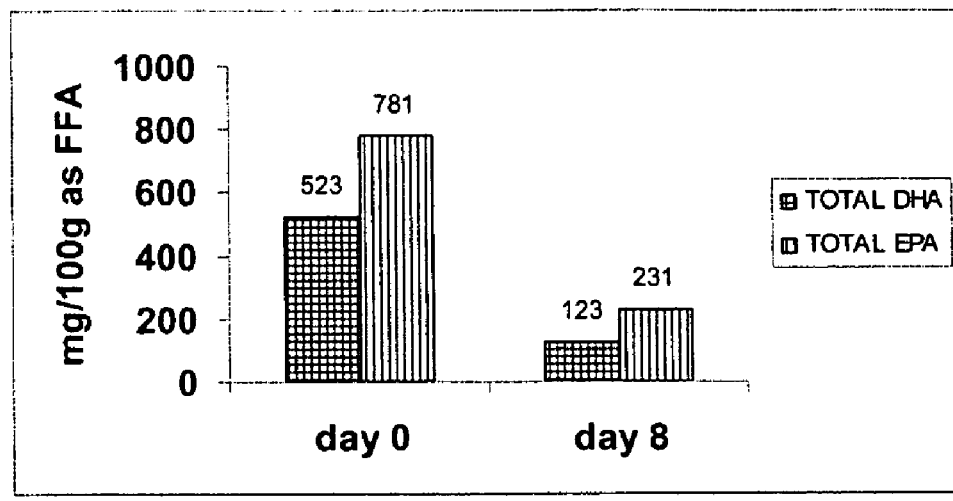
FIG. 6A is a graph illustrating the incorporation of essential fatty acid used to fortify fenugreek into fenugreek sprouts 0 and 8 days after germination, using saponified fish oil as the source of the EFA.

As seen in FIG. 6A, after 8 days of germination, fenugreek sprouts retained some DHA and EPA, even though no remnant of the seed was observed on the sprout. These results indicate that some of the essential fatty acid added to the seed is available to be used by the resulting sprout.

Figure 6B:
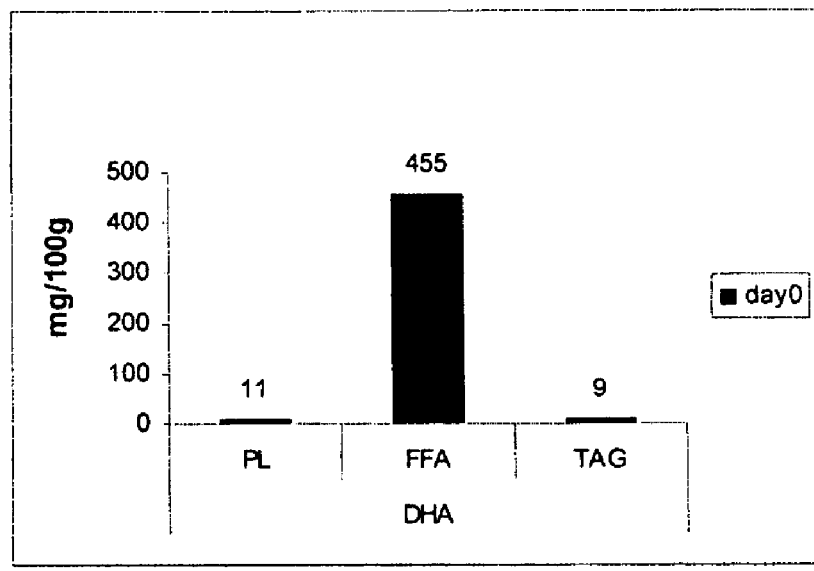
FIG. 6B illustrates the distribution of DHA from saponified fish oil into free fatty acid (FFA), triacylglycerol (TAG) and phospholipid (PL) forms in fenugreek 0 days after germination.
Figure 6C:
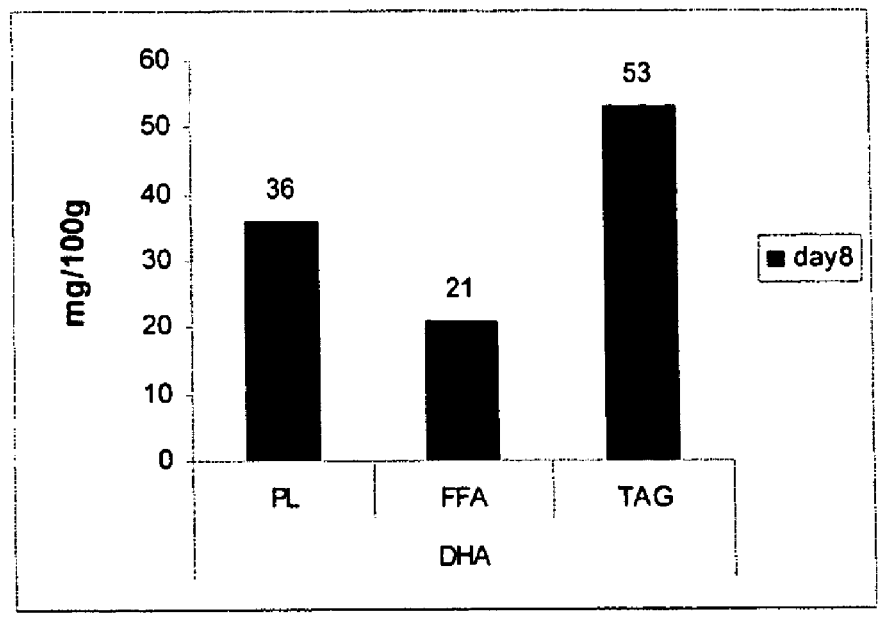
FIG. 6C illustrates the distribution of DHA from saponified fish oil into free fatty acid (FFA), triacylglycerol (TAG) and phospholipid (PL) forms in fenugreek 8 days after germination.
Figure 6D:
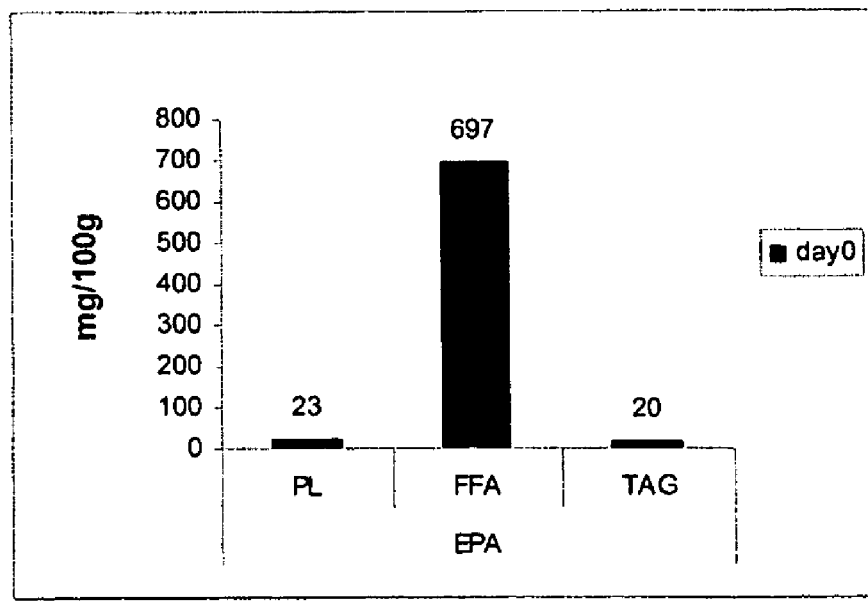
FIG. 6D illustrates the distribution of EPA from saponified fish oil into free fatty acid (FFA), triacylglycerol (TAG) and phospholipid (PL) forms in fenugreek 0 days after germination.
Figure 6E:
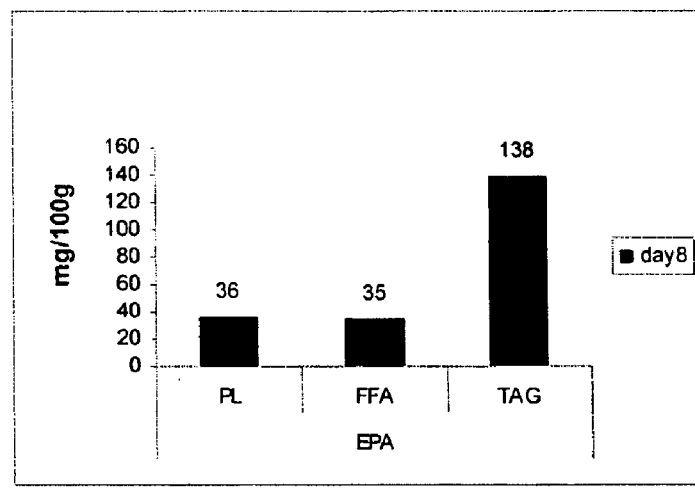
FIG. 6E illustrates the distribution of EPA from saponified fish oil into free fatty acid (FFA), triacylglycerol (TAG) and phospholipid (PL) forms in fenugreek 8 days after germination.
Figure 7A:
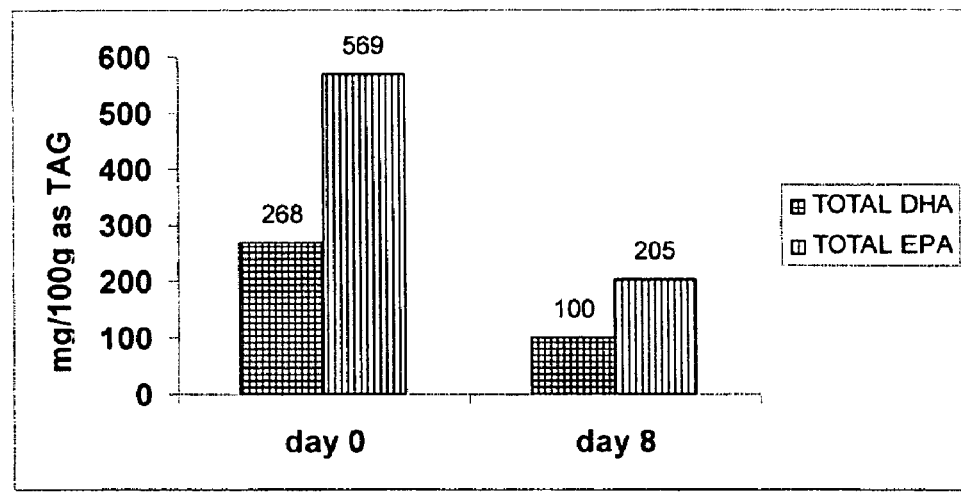
FIG. 7A is a graph illustrating the incorporation of essential fatty acid used to fortify fenugreek into fenugreek sprouts 0 and 8 days after germination, using unsaponified fish oil as the source of the EFA.
Figure 7B:
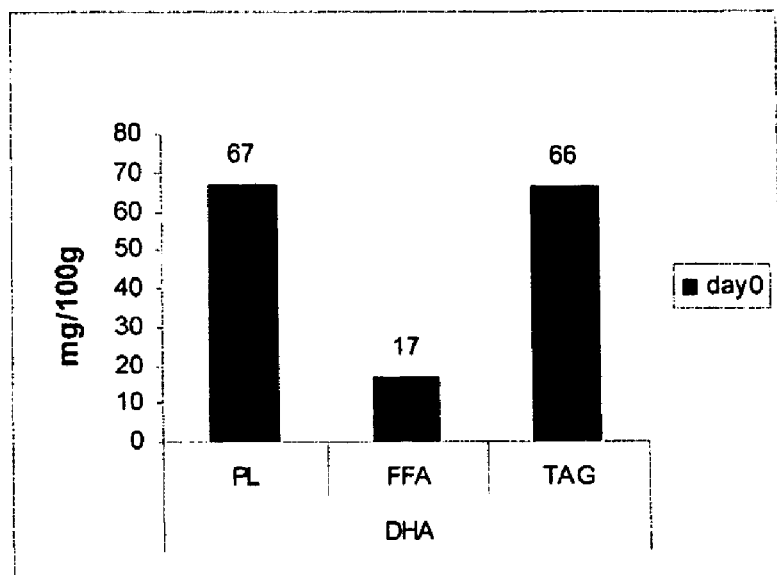
FIG. 7B illustrates the distribution of DHA from unsaponified fish oil into free fatty acid (FFA), triacylglycerol (TAG) and phospholipid (PL) forms in fenugreek 0 days after germination.
Figure 7C:
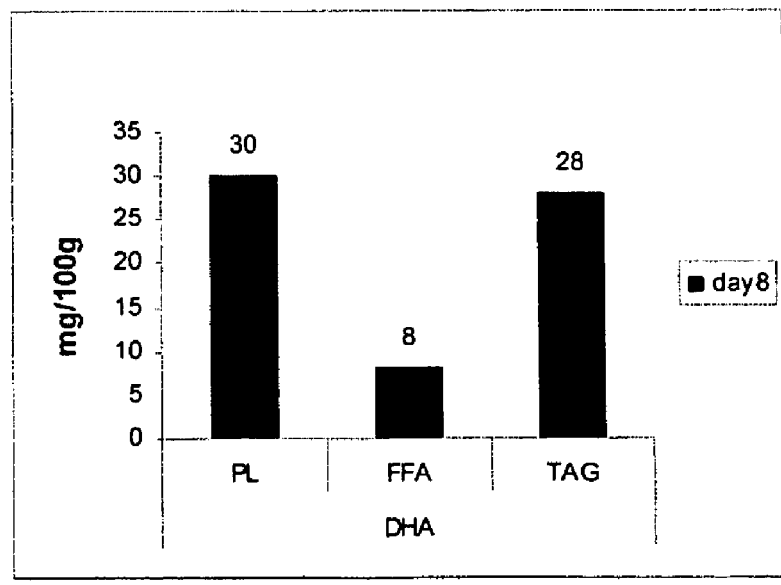
FIG. 7C illustrates the distribution of DHA from unsaponified fish oil into free fatty acid (FFA), triacylglycerol (TAG) and phospholipid (PL) forms in fenugreek 8 days after germination.
Figure 7D:
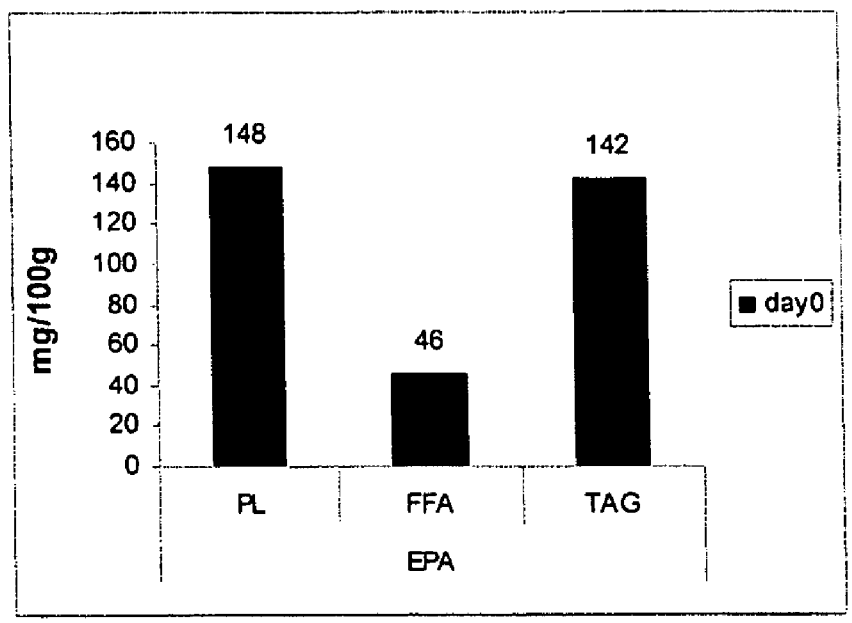
FIG. 7D illustrates the distribution of EPA from unsaponified fish oil into free fatty acid (FFA), triacylglycerol (TAG) and phospholipid (PL) forms in fenugreek 0 days after germination.
Figure 7E:
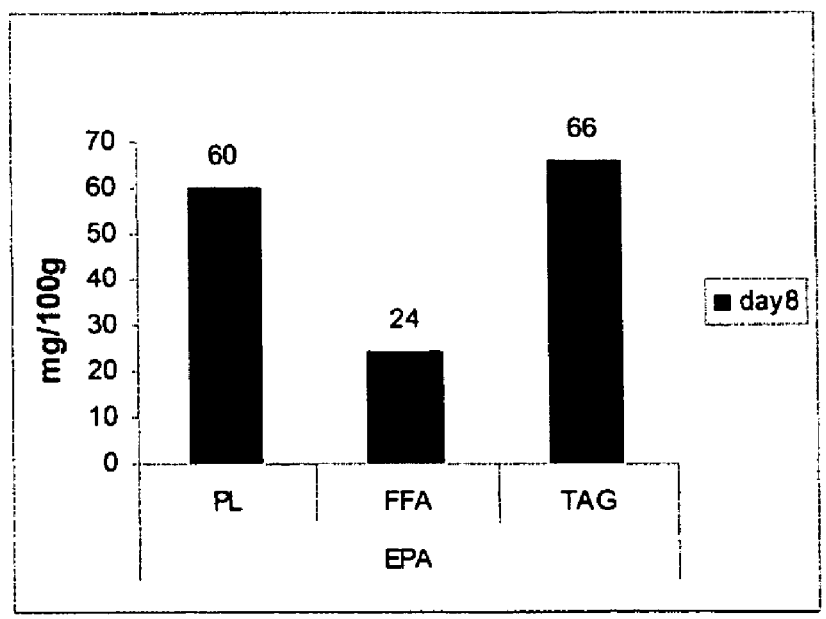
FIG. 7E illustrates the distribution of EPA from unsaponified fish oil into free fatty acid (FFA), triacylglycerol (TAG) and phospholipid (PL) forms in fenugreek 8 days after germination.

Furthermore, analysis of the DHA and EPA content of the germinated seeds indicated that the EFA was available for utilization by the sprout. FIGS. 6B-6E display results obtained using saponified fish oil, in which the DHA and EPA were mostly in the FFA form, with some residual TAG or phospholipid form present (FIGS. 6B and 6D). After 8 days, about 23 to 30% of the total DHA or EPA was retained in the sprouted fenugreek, with a considerable amount of the FFA form processed into TAG or phospholipid form (FIGS. 6C and 6E).

Similar experiments were done using unsaponified fish oil (FIGS. 7A-7E). With the intact FO, a higher percentage of the EFA appeared to be retained by the sprout (36-37%), although there was little or no change in the relative distribution of the forms of the EFA, since the fish oil contains mostly TAG and phospholipid forms of DHA and EPA.

All technical and scientific terms used herein have the same meaning as commonly understood by one of ordinary skill in the art of this invention, unless defined otherwise. Although various embodiments of the present methods and seed are disclosed herein, many adaptations and modifications may be made within the scope of the methods and seed in accordance with the knowledge of those skilled in this art.

What is claimed is:

1. A method of fortifying seed with a polyunsaturated essential fatty acid, comprising: mixing a quantity of said polyunsaturated essential fatty acid with water to form a mixture, wherein said polyunsaturated essential fatty acid is in the form of a free fatty acid or an acylglycerol and is selected from the group consisting of alpha-linolenic acid, docosahexaenoic acid, eicosapentaenoic acid, docosapentaenoic acid, stearidonic acid, linoleic acid, arachidonic acid, gamma-linolenic acid and dihomo gamma-linolenic acid; soaking said seed in said mixture for between 0.5 and 72 hours so that an amount of said polyunsaturated essential fatty acid is absorbed by said seed, said amount of said polyunsaturated essential fatty acid absorbed by said seed being between 10 mg and 1500 mg per 100 g of said seed.

2. The method of claim 1 further comprising dissolving said quantity of said polyunsaturated essential fatty acid in a solvent prior to forming said mixture.

3. The method of claim 2 wherein said solvent is an organic solvent.

4. The method of claim 2 wherein said mixing comprises mixing said solvent containing said polyunsaturated essential fatty acid and water in a ratio of between about 1:99 and about 60:40 of solvent containing said polyunsaturated essential fatty acid:water.

5. The method of claim 4 wherein said mixture has a concentration of said polyunsaturated essential fatty acid of between about 0.001% and about 35%.

6. The method of claim 4 wherein said mixture has a concentration of said polyunsaturated essential fatty acid of between about 0.15% and about 20%.

7. The method of claim 2 wherein said solvent is an emulsifier.

8. The method of claim 1 wherein said polyunsaturated essential fatty acid is in a free fatty acid form.

9. The method of claim 1 wherein said free fatty acid form is obtained by saponification of an acyl glycerol form.

10. The method of claim 1 wherein said amount of said polyunsaturated essential fatty acid that is absorbed by said seed is between 100 mg and 1000 mg per 100 g of said seed.

11. The method of claim 1 wherein said polyunsaturated essential fatty acid is selected from the group consisting of docosahexaenoic acid and eicosapentaenoic acid.

12. The method of claim 1 wherein said seed is selected from the group consisting of flax, fenugreek, edible beans, chick pea, kidney bean, soya bean, nuts, peanut, walnut, almond, white rice, brown rice, wild rice, oats, wheat, corn, barley, hemp, rye, canola, sesame, millet, alfalfa, spelt, amaranth, kamut, quinoa, sorgum, buckwheat, wheat germ, wheat bran, rice bran, oat bran, cumin, oatmeal, popcorn, oil seed, pulses, legumes and lentils.

13. The method of claim 3 wherein said solvent is ethanol.

14. The method of claim 1 wherein said soaking is performed for between 1 and 24 hours.

15. The method of claim 1 wherein said soaking is performed in a volume of said mixture that is between 0.5 and 10 times the volume of said seed.

16. The method of claim 1 wherein said soaking is performed in a volume of said mixture that is between 2 and 5 times the volume of said seed.

17. The method of claim 1 further comprising draining and washing said seed after said soaking.

18. The method of claim 17 further comprising drying said seed after said washing.

19. The method of claim 18 further comprising grinding said seed.

20. The method of claim 1 further comprising germinating said seed.

21. The method of claim 20 wherein said germinating is performed for between 12 and 72 hours.

22. The method of claim 20 further comprising sprouting said seed after germinating.

23. The method of claim 1 further comprising adding an emulsifier.

24. The method of claim 23 wherein said emulsifier is selected from the group consisting of lyso-lecithin, lecithin and t-octylphenoxypolyethoxyethanol.

25. The method of claim 1 further comprising adding an antioxidant.

26. The method of claim 25 wherein said antioxidant is selected from the group consisting of Vitamin C, Vitamin L, tocopherol, anothocyanin, resveratrol, lycopene, pycnogenol, isoflavone, lutein, and carotenoid.

27. The method of claim 1 further comprising saponifying an acylglycerol containing the polyunsaturated essential fatty acid prior to mixing so as to produce a free fatty acid form of said polyunsaturated essential fatty acid.

28. A method of fortifying rice grain with a polyunsaturated essential fatty acid, comprising: dissolving a quantity of said polyunsaturated essential fatty acid in ethanol, wherein in said polyunsaturated essential fatty acid is in free fatty acid form and is selected from the group consisting of docosahexaenoic acid and eicosapentaenoic acid; mixing said ethanol containing said polyunsaturated essential fatty acid with water in a ratio of between about 1:99 and about 60:40 of ethanol containing said polyunsaturated essential fatty acid: water to form a mixture, said quantity of said polyunsaturated essential fatty acid being sufficient to provide a final concentration in said mixture of between about 0.001% and 35%; soaking said rice grain in said mixture for between 0.5 and 72 hours so that an amount of said polyunsaturated essential fatty acid is absorbed by said rice grain, said amount of said polyunsaturated essential fatty acid absorbed by said rice grain being between 10 mg and 1500 mg per 100 g of said rice grain.

29. A seed that is fortified with a polyunsaturated essential fatty acid that is in the form of a free fatty acid or an acylglycerol and is selected from the group consisting of alpha-linolenic acid, docosahexaenoic acid, eicosapentaenoic acid, docosapentaenoic acid, stearidonic acid, linoleic acid, arachidonic acid, gamma-linolenic acid and dihomo gamma-linolenic acid, wherein between 10 mg and 1500 mg of said polyunsaturated essential fatty acid has been absorbed per 100 g of said seed.

30. The seed of claim 29 wherein said polyunsaturated essential fatty acid is in a free fatty acid form.

31. The seed of claim 29 wherein said seed comprises between 100 mg and 1000 mg of said polyunsaturated essential fatty acid per 100 g of said seed.

32. The seed of claim 29 wherein said polyunsaturated essential fatty acid is selected from the group consisting of docosahexaenoic acid and eicosapentaenoic acid.

33. The seed of claim 29 wherein said seed is selected from the group consisting of flax, fenugreek, edible beans, chick pea, kidney bean, soya bean, nuts, peanut, walnut, almond, white rice, brown rice, wild rice, oats, wheat, corn, barley, hemp, rye, canola, sesame, millet, alfalfa, spelt, amaranth, kamut, quinoa, sorgum, buckwheat, wheat germ, wheat bran, rice bran, oat bran, cumin, oatmeal, popcorn, oil seed, pulses, legumes and lentils.

34. The seed of claim 29 that is dried.

35. The seed of claim 34 that is powdered.

36. The seed of claim 29 that has been germinated.

37. The seed of claim 36 that has been sprouted.

38. The seed of claim 29, wherein said seed is fortified by soaking said seed in a mixture containing said polyunsaturated essential fatty acid for between 0.5 and 72 hours.

39. The seed of claim 38, wherein said mixture has a concentration of said polyunsaturated essential fatty acid of between about 0.001% and about 35%.

40. The seed of claim 39, wherein said mixture has a concentration of said polyunsaturated essential fatty acid of between about 0.15% and about 20%.

41. The seed of claim 38 wherein said mixture further comprises an antioxidant.

42. The seed of claim 41 wherein said antioxidant is selected from the group consisting of Vitamin C, Vitamin L, tocopherol, anothocyanin, resveratrol, lycopene, pycnogenol, isoflavone, lutein, and carotenoid.

43. A food product for consumption by an animal, formed at least in part using a seed according to claim 29.

44. The food product of claim 43, wherein said animal is selected from the group consisting of a human, a dog, a cat and a bird.

45. The food product of claim 43, wherein said seed is between about 1% and about 35% (w/w) of said food product.

46. The food product of claim 43 that is selected from the group consisting of breakfast cereal, bread, bread mix, pasta, cookie, cookie mix, cake, cake mix, nutrition bar, meal replacement powder, meal replacement mix, nutrition supplement, pancake mix, waffle mix, chocolate bar, snack bar, animal feed and pet food.

47. The food product of claim 43, where in said polyunsaturated essential fatty acid is in a free fatty acid form.

48. The food product of claim 43, wherein said polyunsaturated essential fatty acid is selected from the group consisting of docosahexaenoic acid and eicosapentaenoic acid.

49. The food product of claim 43, wherein said seed is flax seed.

50. The food product of claim 49, wherein said seed is powdered.

51. The food product of claim 50 that is bread, wherein said seed is between about 2% and about 20% (w/w) of said food product.

52. The food product of claim 50 that is a cookie, wherein said seed is between about 2% and about 35% (w/w) of said food product.

53. A food product for consumption by an animal, formed at least in part using the seed of claim 38.

54. The seed of claim 38, wherein said mixture comprises a solvent and water, said solvent containing said polyunsaturated essential fatty acid.

55. The seed of claim 54, wherein said solvent is ethanol.

56. The seed of claim 54, wherein said mixture further comprises an emulsifier.

57. The seed of claim 54, wherein said solvent is an emulsifier.

58. The seed of claim 57, wherein said emulsifier is selected from the group consisting of lyso-lecithin, lecithin and t-octylphenoxypolyethoxyethanol.

59. The seed of claim 54, wherein said mixture comprises said solvent containing said polyunsaturated essential fatty acid and water in a ratio of between about 1:99 and about 60:40 of solvent containing said polyunsaturated essential fatty acid:water.

* * * * *

UNITED STATES PATENT AND TRADEMARK OFFICE
CERTIFICATE OF CORRECTION

PATENT NO. : 7,416,752 B2  Page 1 of 1
APPLICATION NO. : 10/916336
DATED : August 26, 2008
INVENTOR(S) : Bruce J. Holub and Arun Nagpurkar It is certified that error appears in the above-identified patent and that said Letters Patent is hereby corrected as shown below:

Claim 26, Column 14, line 59, after "Vitamin C" please delete "Vitamin L" and insert -- Vitamin E --.

Claim 42, Column 16, line 4, after "Vitamin C" please delete "Vitamin L" and insert -- Vitamin E --.

Signed and Sealed this

Fourth Day of November, 2008

JON W. DUDAS
*Director of the United States Patent and Trademark Office*